United States Patent [19]

Bergeron

[11] Patent Number: 4,932,869

[45] Date of Patent: Jun. 12, 1990

[54] METHOD OF MAKING DENTURES

[76] Inventor: Claude A. Bergeron, Suite 1002, 151 La Rose Avenue, Weston, Ontario, Canada, M9P 1B3

[21] Appl. No.: 236,246

[22] Filed: Aug. 25, 1988

[51] Int. Cl.5 .............................................. A61C 11/00
[52] U.S. Cl. ..................................... 433/213; 433/167
[58] Field of Search ............... 433/213, 171, 167, 223; 264/16, 17, 18

[56] References Cited

U.S. PATENT DOCUMENTS 4,158,915 6/1979 Stengel ................................. 433/191

Primary Examiner—Cary E. Stone
Attorney, Agent, or Firm—Sim & McBurney

[57] ABSTRACT

The problem of ill-fitting dentures is cured by providing a compensating spacer on the surface of the stone model corresponding to the outside of the alveolar ridge to compensate for inwardly-directed shrinkage of the denture upon release from the stone model.

10 Claims, 3 Drawing Sheets

METHOD OF MAKING DENTURES

FIELD OF INVENTION

The present invention relates to the field of dentistry and, in particular, to a novel method of fitting dentures to a high degree of accuracy.

BACKGROUND TO THE INVENTION

A continuing problem with dentures is that they lack a proper fit in a patient's mouth, causing moderate to severe discomfort to all patients, and such dimensional inaccuracies generally are responsible for inadequate retention of most new dentures.

In the conventional fitting of dentures, a stone model of the contour of the mouth of the patient first is made and thereafter, the denture is molded and cured to the shape of the stone model. Since the stone model corresponds to the shape of the mouth of the patient, it would be expected that the molded denture would accurately fit the mouth of the patient, but this is not the case.

SUMMARY OF INVENTION

I have surprisingly found that, upon release of the denture from the stone model, shrinkage of the denture material occurs which results in the denture material not accurately seating in the alveolar sulcus but rather bearing against the outside of the alveolar ridge, thereby causing pain as a result of the pressure so produced, and, in the case of an upper denture, being spaced from the palate, giving rise to inadequate retention.

With modern denture resins, it is not possible to avoid this shrinkage. In accordance with the present invention, however, accurate-fit dentures may be provided by providing a compensating spacer on selected faces of the stone model. In the case of an upper denture, the compensating spacer is provided on the faces of the stone model corresponding to the outside of the alveolar ridge and corresponding in thickness to the shrinkage of the denture. Upon removal of the denture from the stone model, shrinkage of the denture material results in an accurate fit of the denture to the palate and the alveolar sulcus. In the case of a lower denture, the compensating spacer is provided on the faces of the stone model corresponding to both the outside and inside of the alveolar ridge.

DESCRIPTION OF PREFERRED EMBODIMENT

Figure 2:
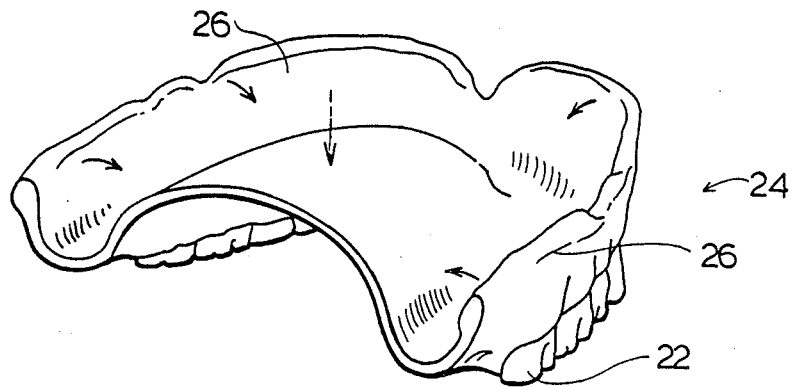
FIG. 2 is a perspective view of a denture, illustrating the shrinkage which occurs after removal from the stone model.
Figure 1:
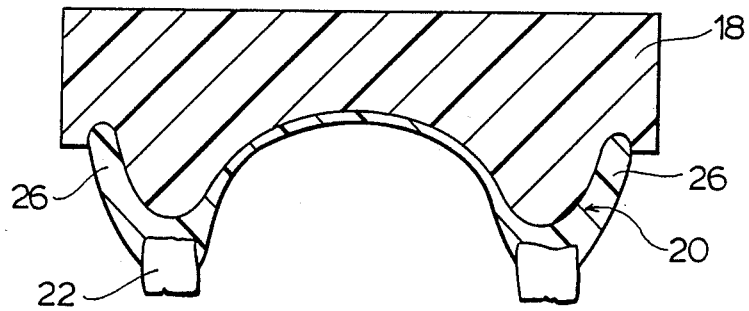
FIG. 1 is a cross-sectional view of the formation of a denture in accordance with conventional practice using a stone model of the roof of a mouth to be fitted with dentures.

Referring to the drawings, the mouth 10 of a patient to be fitted with dentures and include the palate 12, alveolar ridges 14 and alveolar sulcus 16. The first step in the formation of the denture is the formation of a stone model 18 of the mouth 10 of the patient. Next denture material 20, generally a curable polymeric material, is molded to the stone model 18 so as to follow its contours in the desired thickness, while artificial teeth 22 are adhered to the denture material in the locations of the missing teeth of the patient.

The denture material 20 is cured while on the stone model 18 and, at that time, corresponds exactly to the mouth 10 of the patient. However, upon removal of the cured denture 24 from the stone model 18 a small degree of shrinkage of the denture 24 occurs, particularly in the outer flanges 26 which tend to move towards each other (see FIG. 2).

Figure 3:
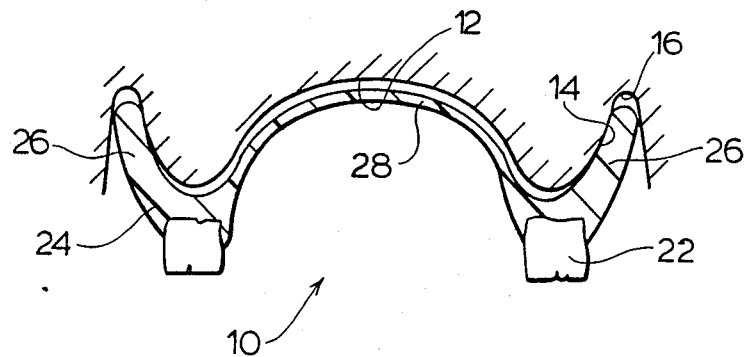
FIG. 3 is a cross-sectional view of the fitting of a denture formed by the conventional procedure of FIG. 1.

The result of this shrinkage is seen in FIG. 3. As may be seen, the flanges 26 of the denture 24 do not seat fully in the alveolar sulcus 16 and the palatal section of the denture base 28 is spaced from the palate 12. The resulting spaces cause a poor retention of the denture 24. At the same time, the flanges 26 bear against the alveolar ridges 14, causing pain and discomfort when biting down on the denture.

The shrinkage of the denture 24 is unavoidable, being an inherent property of the resins which are employed to form the denture material. In my invention, what I seek to do is to permit this shrinkage to result in a denture which exactly conforms to the contour of the mouth 10 of the patient.

Figure 4:
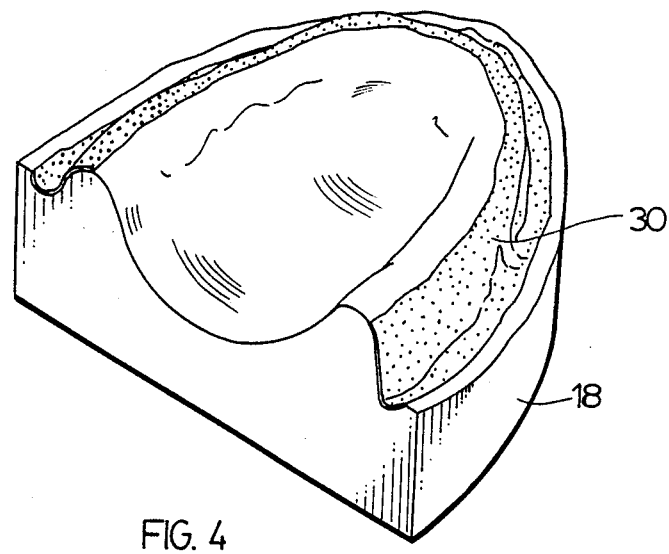
FIG. 4 is a perspective view of a stone model of the roof of a mouth to be fitted with dentures modified in accordance with one embodiment of the invention.

As seen in FIG. 4, this is effected, for an upper denture, by providing a coating 30 on the stone model 18 of a thickness and at a location such that, upon removal of the cured denture 24 from the stone model 18, the resulting inherent shrinkage produces a denture having the necessary fit. For this reason, the coating 30 may be termed a compensating spacer.

Figure 6:
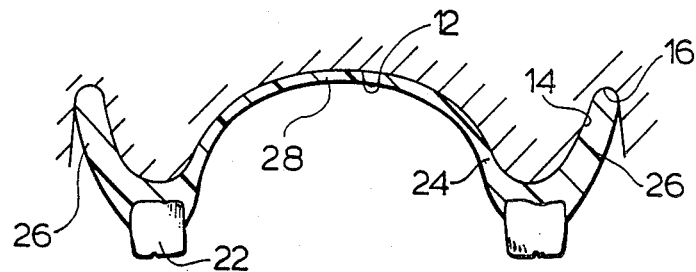
FIG. 6 is a cross-sectional view of the fitting of a denture formed by the procedure of FIG. 5 in the mouth of FIG. 1.

As may be seen from FIG. 6, the result of the provision of the compensating spacer 30 is that the flanges 26 of the palatal section of the denture 24 fit perfectly in the alveolar sulcus 16 and the denture base 28 fits perfectly to the palate 12 of the mouth 10 of the patient. In this way, the denture 24 exhibits a much improved retention. At the same time, the flanges 26 do not bear against the alveolar ridges 14 but rather simply snugly abut the same, so that the pain and discomfort resulting from the arrangement seen in FIG. 3 is eliminated.

Figure 7:
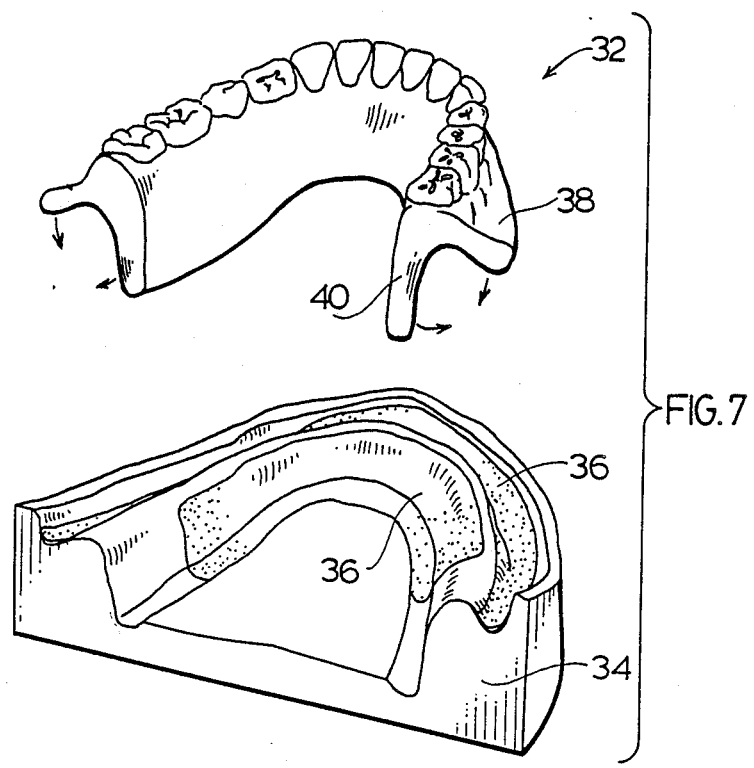
FIG. 7 is a perspective view of the formation of a lower denture using the procedure of the invention.

FIG. 7 illustrates the application of the principles of the invention to a lower denture. In this case, the stone model 34 is provided with a compensating spacer 36 both on the outer and inner surfaces of the portion of the model 34 corresponding to the alveolar ridge, although the inner surface requires only a portion thereof to be coated. Such compensating spacers 36 then compensate for the shrinkages of both flanges 38 and 40 of the denture 32 when it is removed from the stone mold 34.

Figure 5:
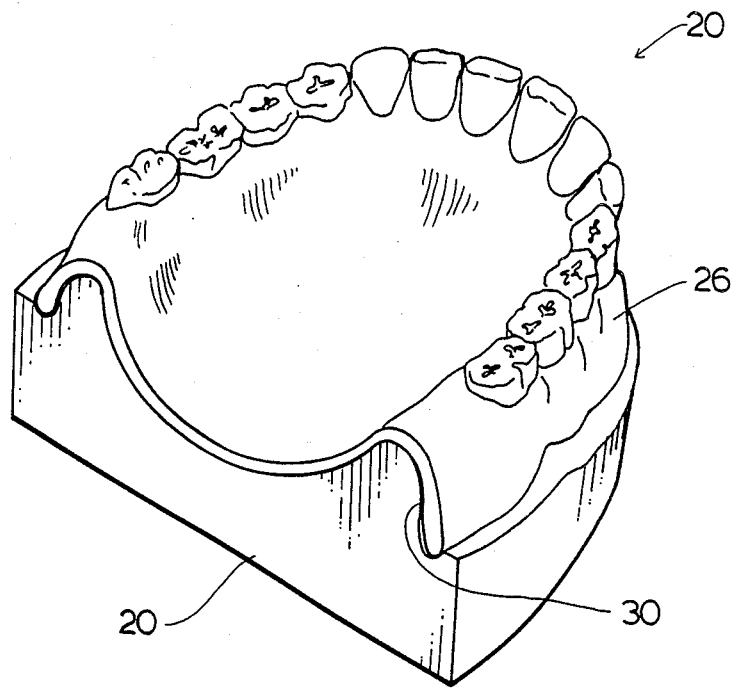
FIG. 5 is a perspective view of the formation of a denture using the stone model of FIG. 4.

In FIG. 5, the coating 30 extends from the apex of the portion of the stone model 18 corresponding to the alveolar ridge to and into the portion of the stone model 18 corresponding to the alveolar sulcus and also for the whole length thereof. In FIG. 7, the coating 36 also is provided on the inner surface but extending only for part of the length. These arrangements are only two of many variations of the principle of providing a compensating spacer in locations and thicknesses corresponding to the expected shrinkage. The thickness of the spacer is important and must be matched to the amount of shrinkage produced by the particular denture base material and processing methods used. Knowing the principle involved, as described herein, the required thickness and location of the compensating spacer is readily determined by those skilled in the art.

Any desired material may be employed to provide the compensating spacer, for example, a curable liquid resin which may be painted on and then cured to solid form, with multiple coats being applied, as required. Such coats may be applied of different colored resins in a particular sequence, each to the same thickness, so that by observing the color, the thickness would be known. Alternatively, resins or paints of different viscosities may be applied to obtain different thicknesses of coatings.

Such material may be rapid drying and preferably is strongly adherent to the stone model, while readily releasing the denture material. Alternatively, a separator may be provided to effect such release.

Another preferred feature of such material is a resistance to boiling temperatures, in order to facilitate the process of wax elimination during denture fabrication.

While the use of curable liquid resins is the simplest and most effective way currently known to me for putting my invention into effect, nevertheless, it is also possible to employ sheet materials, such as lead or tin foil, which are conformable to the shape of the stone model and can provide the required spacing.

The invention is broadly applicable to the fabrication of all types of removable denture prostheses, including complete and partial dentures, overdentures, maxillofacial prosthesis, tissue covering implant dentures as well as in the relining and rebasing of old dentures.

In tests I have carried out using my invention, I have been able to produce dentures which are 17 to 21 times more accurate in fit than those produced by conventional methods.

SUMMARY OF DISCLOSURE

In summary of this disclosure, the present invention provides a novel method of producing dentures which more accurately fit the mouth of a patient than has heretofore been achieved, thereby improving denture retention and decreasing pain and discomfort. Modifications are possible within the scope of this invention.

I claim:

1. In a method for the fabrication of dentures by forming a stone model of the shape of the mouth of a patient to be fitted with dentures and molding the denture to the shape of the stone model, the improvement which comprises directly modifying selected surfaces of said stone model to effect compensation for shrinkage of said denture which occurs after removal from said stone model so as to provide a denture which fits to the shape of the mouth of the patient.

2. In a method for the fabrication of dentures by forming a stone model of the shape of the mouth of a patient to be fitted with dentures and molding the denture to the shape of the stone model, the improvement which comprises modifying selected surfaces of said stone model to effect compensation for shrinkage of said denture which occurs after removal from said stone model by increasing the thickness of selected portions of said stone model so as to provide a denture which fits to the shape of the mouth of the patient.

3. The method of claim 2 wherein said portions of said stone model include that corresponding to the alveolar ridge of the mouth of the patient.

4. The method of claim 3 wherein said portions of said stone model include a portion of the alveolar ridge of the mouth of the patient.

5. The method of claim 4 wherein the denture is a complete upper denture and said portions of said stone model having increased thickness comprise that portion of the stone model extending for the length of the outer portion of the alveolar ridge of the mouth of a patient and extending from the apex of the ridge into the alveolar sulcus.

6. The method of claim 4 wherein the denture is a complete lower denture and said portions of said stone model having increased thickness comprise that portion of the stone model extending for the length of the outer portion of the alveolar ridge of the mouth of a patient and extending from the apex of the ridge into the alveolar sulcus and for a portion of the length of the alveolar ridge of the mouth of a patient and extending for the height thereof.

7. The method of claim 2 wherein said thickness is increased by applying a coating of solid adherent material to said selected portions of said stone model.

8. The method of claim 7 wherein said coating of solid adherent material is applied as a liquid coating of a curable resin, curing the resin to a solid and, as necessary, repeating the steps of application and curing until the desired coating thickness is formed.

9. The method of claim 8, wherein said cured resin is strongly adherent to the stone model but readily releases from the material of fabrication of the denture.

10. The method of claim 7 wherein said coating is provided by a liquid material which is rapidly dried to an adherent coating which is resistant to boiling temperatures.

* * * * *